United States Patent [19]

Kees

[11] Patent Number: 5,688,821
[45] Date of Patent: Nov. 18, 1997

[54] UNSATURATED FATTY ACYL DERIVATIVES OF 2-AMINOTHIAZOLEACETIC ACID AND THEIR SALTS AS INHIBITORS OF PHOSPHOLIPASE $A_2$ DERIVED FROM HUMAN SOURCES

[75] Inventor: Kenneth Lewis Kees, Glennmoore, Pa.

[73] Assignee: American Home Products Corporation, Madison, N.J.

[21] Appl. No.: 771,742

[22] Filed: Dec. 20, 1996

Related U.S. Application Data

[60] Provisional application No. 60/009,332, Dec. 12, 1995.

[51] Int. Cl.$^6$ .................... C07D 277/46; A01K 31/425
[52] U.S. Cl. ............................. 514/371; 548/195
[58] Field of Search ................... 548/195; 514/371

[56] References Cited

U.S. PATENT DOCUMENTS 4,954,489  9/1990  Ponsford .

*Primary Examiner*—Robert Gerstl
*Attorney, Agent, or Firm*—R. F. Boswell, Jr.

[57] ABSTRACT

This invention relates to compounds of the formula

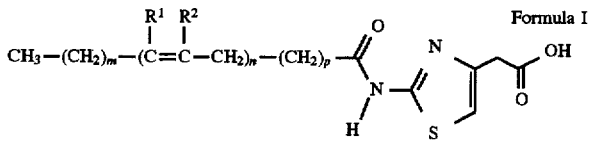

Formula I where $R^1$ and $R^2$ are both hydrogen or $R^1$ and $R^2$ form a bond;

m=1 and n=3 and p=6, or m=3, 5 or 7 and n=1 and p=6, or m=4 and n=2 and p=6 or 8, and the E (trans) and Z (cis) isomers when $R^1=R^2=H$;

and the basic addition salts thereof which are inhibitors of phospholipase $A_2$ and are thus useful agents in the treatment of inflammatory diseases where arachidonic acid metabolic products are implicated, such as rheumatoid arthritis, inflammatory bowel diseases such as ulcerative colitis, atopic dermatitis conditions such as psoriasis and immediate hypersensitivity reactions such as allergic bronchial asthma and allergic rhinitis; and as gastric cytoprotective agents.

17 Claims, No Drawings

UNSATURATED FATTY ACYL DERIVATIVES OF 2-AMINOTHIAZOLEACETIC ACID AND THEIR SALTS AS INHIBITORS OF PHOSPHOLIPASE $A_2$ DERIVED FROM HUMAN SOURCES

This application claims priority to the U.S. provisional application Ser. No. 60/009,332 filed Dec. 28, 1995.

FIELD OF THE INVENTION

This invention relates to novel unsaturated fatty acid carboxamide derivatives of 2-aminothiazoleacetic acid and their salts which are inhibitors of phospholipase $A_2$ and thus inhibit the hydrolysis of arachidonic acid from phospholipids which is metabolized further in the well known arachidonic acid cascade. Some of the metabolic products of arachidonic acid are pro-inflammatory mediators.

BACKGROUND OF THE INVENTION

Phospholipase $A_2$ ($PLA_2$) enzymes catalyze the hydrolysis of arachidonic acid (AA) which is predominantly found esterified in the sn2 position of membrane glycerophospholipids. Arachidonic acid is subsequently metabolized by both cyclooxygenase and lipoxygenase enzymes resulting in the formation of prostaglandins, thromboxanes, hydroxyeicosatetraenoic acids, leukotrienes and other products which play a major role in the inflammatory response. Availability of free AA through activation of $PLA_2$ is therefore the earliest controlling step in the biosynthesis of the pro-inflammatory lipid mediators. The compounds of this invention are inhibitors of phospholipase $A_2$ ($PLA_2$) derived from human sources and thus reduce the availability of free AA for further metabolism. These compounds therefore are useful agents for the treatment of inflammatory diseases where arachidonic acid metabolic products (eicosanoids) are implicated, such as rheumatoid arthritis, inflammatory bowel diseases such as ulcerative colitis, atopic dermatitis conditions such as psoriasis and immediate hypersensitivity reactions such as allergic bronchial asthma and allergic rhinitis; and as gastric cytoprotective agents. (WO 91/06538)

2-Aminothiazoleacetic acid derivatives have been used extensively in chemical and patent literature as intermediates for penam and cepham classes of antibiotics, but the long ($C_{14, 18, 20}$) unsaturated carboxamide chains at $C_2$ of the thiazoleacetic acid heterocycle necessary for this invention makes these compounds novel.

U.S. Pat. No. 5,242,945 (and the corresponding EP 0 508,690 A1) discloses $PLA_2$ inhibiting compounds of the formula

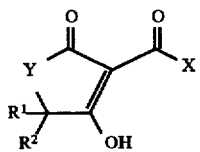

where Y is O or S, $R^1$ and $R^2$ are independently hydrogen or lower alkyl, and X can be $—CH_2$-$(CH_2)_a$-$(CR^3=CR^4)_c$-$(CH_2)_a$-$CH_3$ where $R^3$ and $R^4$ are H or taken together form a bond. These compounds are ketones derived from fatty acids whereas the invention compounds are fatty acid amides of 2-aminothiazol-4-ylacetic acid.

SUMMARY OF THE INVENTION

This invention encompasses compounds of Formula I, methods of treating conditions related to actions of arachidonic acid and its metabolites, and compositions thereof wherein the compounds have the formula

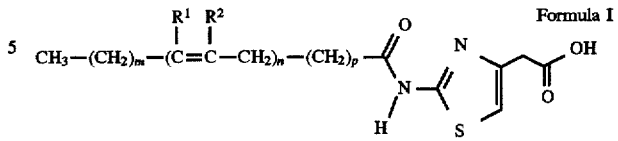

where $R^1$ and $R^2$ are both hydrogen or $R^1$ and $R^2$ form a bond;

m=1 and n=3 and p=6, or m=3, 5 or 7 and n=1 and p=6, or m=4 and n=2 and p=6 or 8, and the E (trans) and Z (cis) isomers when $R^1=R^2=H$ and the pharmaceutically acceptable basic addition salts thereof.

The compounds of this invention are shown in in-vivo and in-vitro assays to inhibit $PLA_2$ either through measurement of reduction of arachidonic acid levels or inhibition of effects of arachidonic acid metabolites and therefore are expected to be useful in the treatment of the inflammatory diseases mediated by the arachidonic acid metabolites.

DETAILED DESCRIPTION OF THE INVENTION

The compounds of this invention are synthesized in a conventional manner by saponification of the corresponding 2-fatty acylaminothiazole-4-acetic acid ethyl esters, followed by acidification of the reaction mixture. The simple esters are inactive. Basic salts of these acids are prepared also in a conventional manner as is known in the art. In particular the tromethamine salts of this invention provide water soluble derivatives for improved bioavailability. The acylaminothiazoleacetic acid esters are prepared in one of two ways: condensation of ethyl-2-aminothiazoleacetate with a fatty acid chloride in the presence of a tertiary amine base such as triethylamine or diisopropylethylamine in an aprotic solvent (e.g. dichloromethane or tetrahydrofuran) at ice temperature (Procedure A) or, preferably, directly from the fatty acid with the aid of an organodiimide coupling agent as is well known in the synthesis of peptides (Procedure B).

EXAMPLE 1 (Procedure A):

2[((Z)-1-Oxo-9-octadecenyl)amino]-4-thiazoleacetic acid

A mixture of ethyl 2-aminothiazoleacetic acid (4.6 g, 24.7 mmol) and triethylamine (4.2 mL, 20.3 mmol) in dichloromethane (125 mL) was cooled in an ice bath under $N_2$ atmosphere. Oleoylchloride (neat, 75%, 11 mL, 25 mmol) was added dropwise and the reaction was then allowed to warm to room temperature. After 15 h at room temperature 10% aqueous HCl solution was added to the reaction mixture, stirred for 2 h and then poured onto saturated aqueous brine solution in a separatory funnel. The organic layer was separated, dried over anhydrous $MgSO_4$, filtered and concentrated on a rotary evaporator to a yellow oil. The crude ester was purified by HPLC (70% hexane, 30% EtOAc) to give 4 g of ethyl-2-[((Z)-1-oxo-9-octadecenyl)amino]-4-thiazoleacetate, as a yellow oil. IR (film) $v(cm^{-1})$: 1745, 1700. MS (EI) m/z 450 ($M^+$).

Ethyl-2-[((Z)-1-oxo-9-octadecenyl)amino]-4-thiazoleacetate (4.00 g, 8.89 mmol), sodium hydroxide (0.79 g, 19.8 mmol) and tetrahydrofuran (50 mL) were combined and cooled in an ice bath under $N_2$ atmosphere. Enough distilled water was added to the mixture to dissolve the hydroxide and provide a homogeneous solution. The reaction was kept at 0° C. for 2 h, then allowed to warm to room temperature and stirred overnight. 10% aqueous HCl solution was added to the mixture, and stirring continued for 1 h. Ethyl acetate and saturated aqueous brine solution were added to the mixture, and the organic phase was separated and dried over $MgSO_4$. After filtration and concentration the crude dark amber oil was treated with ether, stirred for 0.5 h and the product was collected on a Buehner funnel and air dried to give 1.5 g of the title compound as a white solid, mp 106°–108.5° C.

Analysis for: $C_{23}H_{38}N_2O_3S$ Calc'd: C, 65.36; H, 9.06; N, 6.63 Found: C, 64.99; H, 9.19; N, 6.57

EXAMPLE 2: 2-[((Z)-1-Oxo-9-octadecenyl)amino]-4-thizaoleacetic acid, tromethamine (2-amino-2-hydroxymethyl)-1,3-propanediol) salt A mixture of the title compound of Example 1 (4.14 g, 9.8 mmol) and tromethamine (1.2 g, 9.9 mmol) in n-propanol (75 mL) was heated on a steam bath until a homogeneous solution was obtained. The solution was allowed to stand at room temperature for 15 h, then concentrated in vacuo to an amber syrup, which hardened when triturated with warm dichloromethane. The solution was decanted and the residue was dried under vacuum to give 1.4 g of the title compound as a pale yellow hygroscopic wax, mp 155°–157° C.

Analysis for: $C_{27}H_{49}N_3O_6S \cdot 0.25\ H_2O$ Calc'd: C, 59.15; H, 9.19; N, 7.66 Found: C, 58.88; H, 9.26; N, 7.86

EXAMPLE 3 (Procedure B): 2-[((E)-1-Oxo-9-octadecenyl)amino]-4-thiazoleacetic acid A mixture of elaidic acid (5.1 g, 17.7 mmol; 98%), ethyl-2-aminothiazoleacetate (3.3 g, 17.7 mmol), triethylamine (2.8 g, 27.7 mmol), 1-(3-dimethylaminopropyl)-3-ethyl carbodiimide hydrochloride (5.3 g, 26.9 mmol) and 4-dimethylaminopyridine (0.4 g, 3.3 mmol) was combined in dichloromethane (225 mL) at ice temperature under $N_2$ atmosphere. The mixture was stirred at 0° C. for 1 h, then allowed to warm to room temperature and stirred for 15 h. The reaction mixture was diluted with water and the organic phase was separated, washed with water and saturated brine solution, dried over $MgSO_4$, filtered and concentrated to give 7.1 g of ethyl-2-[((E)-1-oxo-9-octadecenyl)-amino]-4-thiazoleacetate, which was used directly without purification.

A mixture of the above ester (7.4 g, 16.5 mmol) and sodium hydroxide (1.44 g, 36.1 mmol) was combined in THF (150 mL) and cooled in ice under $N_2$ atmosphere. Enough distilled water was added portionwise until the hydroxide was dissolved (~15 mL) and the mixture was maintained at 0° for 2 h, then allowed to warm to ambient temperatures with stirring for 15 h. The reaction mixture was evaporated in vaccuo, the residue cooled in ice and treated with 2M aqueous HCl solution with stirring. The whim precipitate was collected by vacuum filtration, washed with water and air dried. This material was crystallized from boiling heptane, filtered hot, and dried overnight on an abderhalden apparatus (refluxing acetone) to give 4.6 g of the title compound as a white powder, mp 116°–118° C.

Analysis for: $C_{23}H_{38}N_2O_3S$ Calc'd: C, 65.37; H, 9.06; N, 6.63 Found: C, 65.33; H, 9.15; N, 6.59

EXAMPLE 4: 2-[(1-Oxo-9-octadecynyl)amino]-4-thiazoleacetic acid

The title compound was prepared by Procedure A (example 1). The crude product was crystallized from hot heptane to give lemon colored crystals, mp 95.5°–96.5° C.

Analysis for: $C_{23}H_{36}N_2O_3S$ Calc'd: C, 65.68; H, 8.63; N, 6.66 Found: C, 65.46; H, 8.53; N, 6.74

EXAMPLE 5: 2-[(1-Oxo-9-octadecynyl)amino]-4-thiazoleacetic acid, tromethamine salt The title compound was prepared from tromethamine and the title compound of Example 4 by the method of Example 2, except that the final product was obtained directly from n-propanol solution by cooling the mixture in ice, followed by vacuum filtration and drying, which provided the title compound as a partially hydrated, pale yellow wax.

Analysis for: $C_{27}H_{47}N_3O_6S \cdot 0.5\ H_2O$ Calc'd: C, 58.88; H, 8.60; N, 7.63 Found: C, 58.73; H, 8.45; N, 7.56

EXAMPLE 6: 2-[((E,E)-1-Oxo-9,12-tetradecadienyl)amino]-4-thiazoleacetic acid The title compound was prepared by procedure B (Example 3). The crude acid was purified by flash chromatography on silica gel (40 wt. eq., elution with ethyl acetate-hexane (60–40)+1% acetic acid) followed by crystallization from heptane, providing the title compound as a waxy white solid, mp 101°–102° C.

Analysis for: $C_{23}H_{36}N_2O_3S$ Calc'd: C, 65.68; H, 8.63; N, 6.66 Found: C, 66.01; H, 8.66; N, 6.58

EXAMPLE 7: 2-[((Z,Z,Z)-1-Oxo-9,12,15-octadecatrienyl)amino]-4-thiazole-acetic acid The title compound was prepared by procedure B and precipitated from heptane as a hygroscopic yellow wax.

Analysis for: $C_{23}H_{34}N_2O_3S \cdot 1.5\ H_2O$ Calc'd: C, 61.99; H, 7.92; N, 6.29 Found: C, 62.22; H, 7.68; N, 6.02

EXAMPLE 8: 2-[((Z)-1-Oxo-9-tetradecenyl)amino]-4-thiazoleacetic Acid

The title compound was prepared by procedure B. The crude acid crystallized from hot heptane as lemon colored crystals, mp 110°–111° C.

Analysis for: $C_{19}H_3ON_2O_3S$ Calc'd: C, 62.26; H, 8.25; N, 7.64 Found: C, 62.06; H, 8.27; N, 7.53

EXAMPLE 9: 2[((Z)-1-Oxo-9-tetradecenyl)amino]-4-thiazoleacetic acid, tromethamine salt The title compound was prepared as in Example 2 from the title compound of Example 8. Pale yellow crystals were obtained by trituration of the amber oil with dichloromethane. mp 92°–95° C.

Analysis for: $C_{23}H_{41}N_3O_6S \cdot 0.25\ H_2O$ Calc'd: C, 55.96; H, 8.66; N, 8.37 Found: C, 56.13; H, 8.60; N, 8.54

EXAMPLE 10: 2[((Z,Z)-1-Oxo-11,14-eicosadienyl)amino]-4-thiazoleacetic acid

The title compound was prepared by the method of example 3 (Procedure B). The product precipitated from boring hexane and was dried under vacuum to give a yellow-orange wax.

Analysis for: $C_{25}H_{40}N_2O_3S$ Calc'd: C, 66.93; H, 8.99; N, 6.24 Found: C, 67.19; H, 8.65; N, 5.96

Pharmacology

The compounds of the invention are tested in an in vitro isolated phospholipase $A_2$ assay to determine the ability of the test compounds to inhibit the release of arachidonic acid from an arachidonic acid-containing substrate by the action of phospholipase A enzyme from two human sources.

1. INHIBITION OF PLA$_2$ DERIVED FROM HUMAN PLATELETS AND HUMAN SYNOVIAL FLUID

This assay is carried out as follows:
Into a 15 mL polypropylene tube are added the following:

| Agent | Volume, μL | Final Conc. |
|---|---|---|
| $^3$H-AA *E. coli* substrate[1] | 25 | 5 nmoles PL |
| CaCl$_2$ (0.1M)[2] | 5 | 5 mM |
| Tris-HCl (0.5M), pH 7.5[3] | 20 | 100 mM |
| Water[4] | 25 | |
| Drug/Vehicle[5] | 1 | 50 μM |
| PLA$_2$ | 25 | volume yielding 12% hydrolysis in 10 min. |

*pre-incubate at room temperature 30 min prior to substrate addition.

[1]. Prepared by adding 2 mL deionized and distilled water to 2 mL $^3$H-arachidonate labeled *E. coli* (lower count), to which is added 1 mL of $^3$H-arachidonate labeled *E. coli* (higher count) to yield a total of 5 mM substrate (containing 1000 nmoles phospholipid, PL).

[2] Stock 0.1M CaCl$_2$ required for enzyme activity.

[3] Stock 0.5M Trisma-Base. Stock 0.5M Trisma-HCl. Adjust pH to 7.5 (optimum for enzyme).

[4] Deionized and distilled water.

[5] Stock 10 mM prepared in dimethyl sulfoxide. Make 1:2 dilution with dimethyl sulfoxide and add 1 μL to 100 μL assay tube.

[6] Two human PLA$_2$ enzymes are used:
  (a) semi-purified human platelet acid extract PLA$_2$ (in 10 mM sodium acetate buffer, pH 4.5). Remove protein precipitate by centrifugation at about 2200 rpm for 10 minutes.
  (b) Purified human synovial fluid.

Incubate the 100 gL reaction mixture for 10 minutes at 37° C. in a shaking water bath. The reaction is terminated by the addition of 2 mL tetrahydrofuran, followed by vortexing. NH$_2$ columns (100 μg/mL—Analytichem International) are conditioned with 0.5 mL tetrahydrofuran followed by 0.5 mL tetrahydrofuran/water (2 mL:0.1 mL, v/v).

The sample is loaded onto the columns and slowly dram through them. The hydrolyzed arachidonic acid retained in the columns is eluted therefrom with 1 mL tetrahydrofuran/ glacial acetic acid (2%). The arachidonic acid is transferred to scintillation vials and quantitated by β-counting analysis. A "total counts" sample is prepared by pipetting 25 μl, $^3$H-arachidonate *E. coli* directly into a scintillation vial to which is added 1 mL tetrahydrofuran. 10 mL aquasol (scintillation cocktail) is added to all samples.

Calculations:

$$\% \text{ hydrolysis} = \frac{[^3H]AA \text{ dpm(sample)} - [^3H]AA \text{ dpm (nonspecific hydrolysis)}}{\text{total counts dpm}} \times 100$$

$$\% \text{ change} = \frac{\text{vehicle dpm} - \text{drug dpm}}{\text{vehicle dpm}} \times 100$$

Activity of Standard Drugs:

| | IC$_{50}$ (μM) | |
|---|---|---|
| Drugs | Human Platelet PLA$_2$ | Human Synovial PLA$_2$ |
| Arachidonic Acid | 8.6 | 3.2 |
| Monoalide | 25.2 | 0.14 |

Representative results obtained for the test compounds of this invention are summarized in Table 1.

TABLE 1

Inhibition of PLA$_2$ Derived from Human Synovial Fluid (HSF) and Human Platelets (HP)

| | % Inhibition (IC$_{50}$) | | Drug |
|---|---|---|---|
| Example | HSF | HP | Concentration (μM) |
| 1 | 96(1.7) | 57.5(27.9) | 50 |
| 2 | 25.9 | 36 | 10 |
| 3 | 81.7(2.1) | 70(25.7) | 50 |
| 4 | 42.5 | 8.9 | 10 |
| 5 | 66 | 26 | 10 |
| 6 | 84.8 | 74.6 | 10 |
| 7 | 38.5 | 0.5 | 10 |
| 8 | 2* | 65.6* | 10 |
| 9 | 26.9 | 74 | 10 |
| 10 | 86.3 | 82.7 | 50 |

*Average of two runs

2. TPA-induced dermal inflammation in mouse ears

Female Swiss Webster mice (Buckshire; 8 weeks old) were divided into groups of six. Tetradecanoylphorbol acetate CrPA) was dissolved in acetone at concentrations of 50 mg/ml and 200 μg/ml, respectively. Each mouse received 4 μg/ear of TPA on the right ear. These suboptimal doses of phlogistics were applied by an automatic pipette in 10 μl volumes to both the inner and outer surfaces of the ear. The left ear (control) received acetone or vehicle. Drags were applied topically in acetone and in some cases 95% ethanol was used to solubilize the drug prior to dilution with acetone. Drags were given 30 min. after treatment (+30 min) with TPA. Edema measurements were taken with an Oditest calipers. The thickness of the right and left ears were usually measured in traits of 0.01 mm 4 h after TPA application. Ear edema was calculated by subtracting the thickness of the left ear (vehicle control) from right ear (treated ear).

| Compd. | Dose (mg/ear) | Route | % Change Edema |
|---|---|---|---|
| Example 3 | 1 | Topical | −22* |
| Example 3 | 1 | Topical | −36* |
| Example 3 | 100 | Topical | −20* |
| WY-47288 (reference 5-LO/CO inhibitor[1]) | 1 | Topical | −40* |

*p ≦0.05

Murine paw edema assay

The assay measures the ability of the compounds of the invention to inhibit paw edema induced by the exogenous administration of PLA$_2$ and is carded out as follows:

Non-fasted, male CD-1 mice (8 weeks old; 31–36 grams) are placed in plastic boxes in groups of six. The right hind paw volume is measured using mercury plethysmography (zero time). Compounds are dosed orally (0.5 mL of 0.5% Tween-80) 1 or 3 hours prior to PLA$_2$ injection or intravenously (0.2 mL in 0.3% dimethylsulfoxide/saline) 3 minutes prior to PLA$_2$ injection. A solution of purified PLA$_2$, from the diamondback cottonmouth snake (*A.piscivorus piscivorus*) is prepared in saline at a concentration of 6 μg/mL. Fifty (50) μL (0.3 μg) of this PLA$_2$ solution is injected subcutaneously into the right-hind paw with a 1 mL plastic syringe (27 gauge, 1" needle). Paw volume of the injected paw is measured again at 10 and 30 minutes after PLA$_2$ injection. Animals are euthanized with $CO_2$ at the completion of the study.

The paw edema is calculated by subtracting the zero time volume from the volume recorded at each time period. Mean paw edema for each treatment group is then calculated and expressed as (μL±S.E.) Drug effects are expressed as a percent change from control (vehicle) values. Statistical significance is determined by a one-way analysis of variance with LSD comparison to control (p<0.05). $ED_{50}$'s are determined using regression analysis.

| Compound | Dose (mg/kg)/route | % change paw edema | |
|---|---|---|---|
| | | 10 min | 30 min |
| Example 3 | 30 i.p. | −33* | −43* |
| WY-47288 (reference LO/CO inhibitor)[1] | | Inactive | |
| Luffariellolide (reference $PLA_2$ inhibitor) | | Inactive | |

*p ≦0.05

References

1. Carlson, R. P.; O'Neill-Davis, L; Calhoun, W; Datko, L; Musser, J. H.; Kreft, A. F.; Chang, J. Y. Agents and Actions, 26, 319 (1989).

Pharmaceutical Composition

Compounds of this invention may be administered neat or with a pharmaceutical carrier to a patient in need thereof. The pharmaceutical carrier may be solid or liquid.

Applicable solid carders can include one or more substances which may also act as flavoring agents, lubricants, solubilizers, suspending agents, fillers, glidants, compression aids, binders or tablet-disintegrating agents or an encapsulating material. In powders, the carder is a finely divided solid which is in admixture with the freely divided active ingredient. In tablets, the active ingredient is mixed with a carder having the necessary compression properties n suitable proportions and compacted in the shape and size desired. The powders and tablets preferably contain up to 99% of the active ingredient. Suitable solid carders include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carder such as water, an organic solvent, a mixture of both or pharmaceutically acceptable oils or fat. The liquid carder can contain other suitable pharmaceutical additives such a solubilizers, emulsifiers, buffers, preservatives, sweeteners, flavoring agents, suspending agents, thickening agents, colors, viscosity regulators, stabilizers or osmo-regulators. Suitable examples of liquid carders for oral and parenteral administration include water (particularly containing additives as above, e.g., cellulose derivatives, preferable sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carder can also be an oily ester such as ethyl oleate and isopropyl myristate. Sterile liquid carders are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

The compounds of this invention may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carder that is inert to the active compound, is non-toxic to the skin, and allows delivery of the agent for systemic absorption into the blood stream via the skin. The carrier may take any number of forms such as creams and ointments, pastes, gels, and occlusive devices. The creams and ointments may be viscous liquid or semi-solid emulsions of either the oil in water or water in oil type. Pastes comprised of absorptive powders dispersed in petroleum or hydrophilic petroleum containing the active ingredient may also be suitable. A variety of occlusive devices may be used to realease the active ingredient into the blood stream such as a semipermeable membrane covering a reservoir containing the active ingredient with or without a carrier, or a matrix containing the active ingredient. Other occlusive devices are known in the literature.

The dosage to be used in the treatment of a specific patient suffering from cerebral acetylcholine insufficiency must be subjectively determined by the attending physician. The variables involved include the severity of the dysfunction, and the size, age, and response pattern of the patient. Treatment will generally be initiated with small dosages less than the optimum dose of the compound. Thereafter the dosage is increased until the optimum effect under the circumstances is reached. Precise dosages for oral, parenteral, nasal, or intrabronchial administration will be determined by the administering physician based on experience with the individual subject treated and standard medical principles.

Preferably the pharmaceutical composition is in unit dosage form, e.g., as tablets or capsules. In such form, the composition is sub-divided in unit dose containing appropriate quantities of the active ingredient; the unit dosage form can be packaged compositions, for example packed powders, vials, ampoules, prefilled syringes or sachets containing liquids. The unit dosage form can be, for example, a capsule or tablet itself, or it can be the appropriate number of any such compositions in package form.

What is claimed is:

1. A compound having the formula

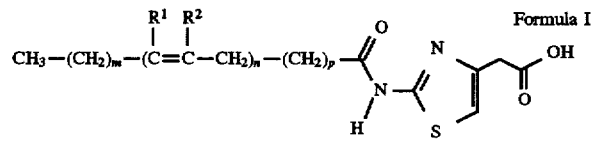

Formula I where $R^1$ and $R^2$ are both hydrogen or $R^1$ and $R^2$ form a bond;

m=1 and n=3 and p=6, or m=3, 5 or 7 and n=1 and p=6, or m=4 and n=2 and p=6 or 8, and the E (trans) and Z (cis) isomers when $R^1=R^2=H$;

or a pharmaceutically acceptable basic addition salt thereof.

2. A compound according to claim 1 which is 2-[((Z)-1-oxo-9-octadecenyl)amino]-4-thiazoleacetic acid.

3. A compound according to claim 1 which is 2-[((Z)-1-oxo-9-octadecenyl)amino]-4-thizaoleacetic acid, tromethamine (2-amino-2-hydroxymethyl)-1,3-propanediol) salt.

4. A compound according to claim 1 which is 2-[((E)-1-oxo-9-octadecenyl)amino]-4-thiazoleacetic acid.

5. A compound according to claim 1 which is 2-[(1-oxo-9-octadecenyl)amino]-4-thiazoleacetic acid.

6. A compound according to claim 1 which is 2-[(1-oxo-9-octadecynyl)amino]-4-thiazoleacetic acid, tromethamine salt.

7. A compound according to claim 1 which is 2-[((EE)-1-oxo-9,12-tetradecadienyl)amino]-4-thiazoleacetic acid.

8. A compound according to claim 1 which is 2-[((Z,Z,Z)-1-oxo-9,12,15-octadecatrienyl)amino]-4-thiazole-acetic acid.

9. A compound according to claim 1 which is 2-[((Z)-1-oxo-9-tetradecenyl)amino]-4-thiazoleacetic acid.

10. A compound according to claim 1 which is 2[((Z)-1-oxo-9-tetradecenyl)amino]-4-thiazoleacetic acid, tromethamine salt.

11. A compound according to claim 1 which is 2[((Z,Z))-1-oxo-11,14-eicosadienyl)amino]-4-thiazoleacetic acid.

12. A method of treating inflammatory diseases mediated by arachidonic acid metabolites which comprises administering to a mammal needing such treatment a phospholipase $A_2$-inhibiting amount of a compound having the formula

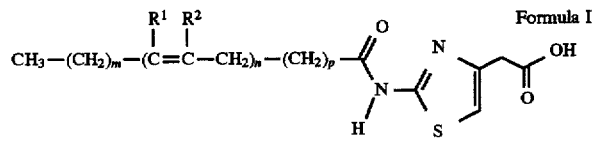

where $R^1$ and $R^2$ are both hydrogen or $R^1$ and $R^2$ form a bond;

m=1 and n=3 and p=6, or m=3, 5 or 7 and n=1 and p=6, or m=4 and n=2 and p=6 or 8, and the E (trans) and Z (cis) isomers when $R^1=R^2=H$;

or a pharmaceutically acceptable basic addition salt thereof.

13. A method of treatment according to claim 12 wherein the inflammatory disease treated is rheumatoid arthritis.

14. A method of treatment according to claim 12 wherein the inflammatory disease treated is ulcerative colitis.

15. A method of treatment according to claim 12 wherein the inflammatory disease treated is psoriasis.

16. A method of treatment according to claim 12 wherein the inflammatory disease treated is allergic bronchial asthma or allergic rhinitis.

17. A pharmaceutical composition which comprises a pharmaceutically acceptable carrier and a therapeutically effective amount of a compound of the formula

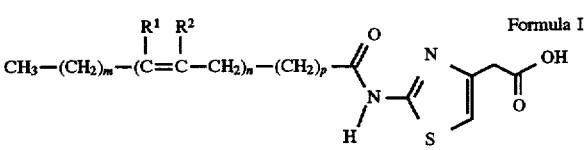

where $R^1$ and $R^2$ are both hydrogen or $R^1$ and $R^2$ form a bond;

m=1 and n=3 and p=6, or m=3, 5 or 7 and n=1 and p=6, or m=4 and n=2 and p=6 or 8, and the E (trans) and Z (cis) isomers when $R^1=R^2=H$;

or a pharmaceutically acceptable basic addition salt thereof.

* * * * *